United States Patent [19]

Gloyer

[11] Patent Number: 4,832,693
[45] Date of Patent: May 23, 1989

[54] DISPOSABLE SYRINGE

[76] Inventor: Walter W. Gloyer, 1010 W. Main St., Tomball, Tex. 77375

[21] Appl. No.: 107,659

[22] Filed: Oct. 9, 1987

[51] Int. Cl.⁴ .............................................. A61M 5/00
[52] U.S. Cl. ..................................... 604/110; 604/238
[58] Field of Search ................ 604/110, 111, 238, 236

[56] References Cited

U.S. PATENT DOCUMENTS 2,893,390  7/1959  Lockhart .............................. 604/238
4,233,975  11/1980  Yerman ................................. 604/110
4,479,801  10/1984  Cohen .................................. 604/238

Primary Examiner—John D. Yasko
Attorney, Agent, or Firm—Guy E. Matthews

[57] ABSTRACT

A single use hypodermic needle syringe is constructed in a manner which provides for the automatic self destruction of the fluid passage during the initial use upon the first complete injection stroke. Because the fluid passage is destroyed upon the first initial use of the hypodermic needle syringe, the syringe is rendered useless and must be discarded. Because the syringe is discarded after one use, the spread of infectious diseases will be inhibited.

7 Claims, 2 Drawing Sheets

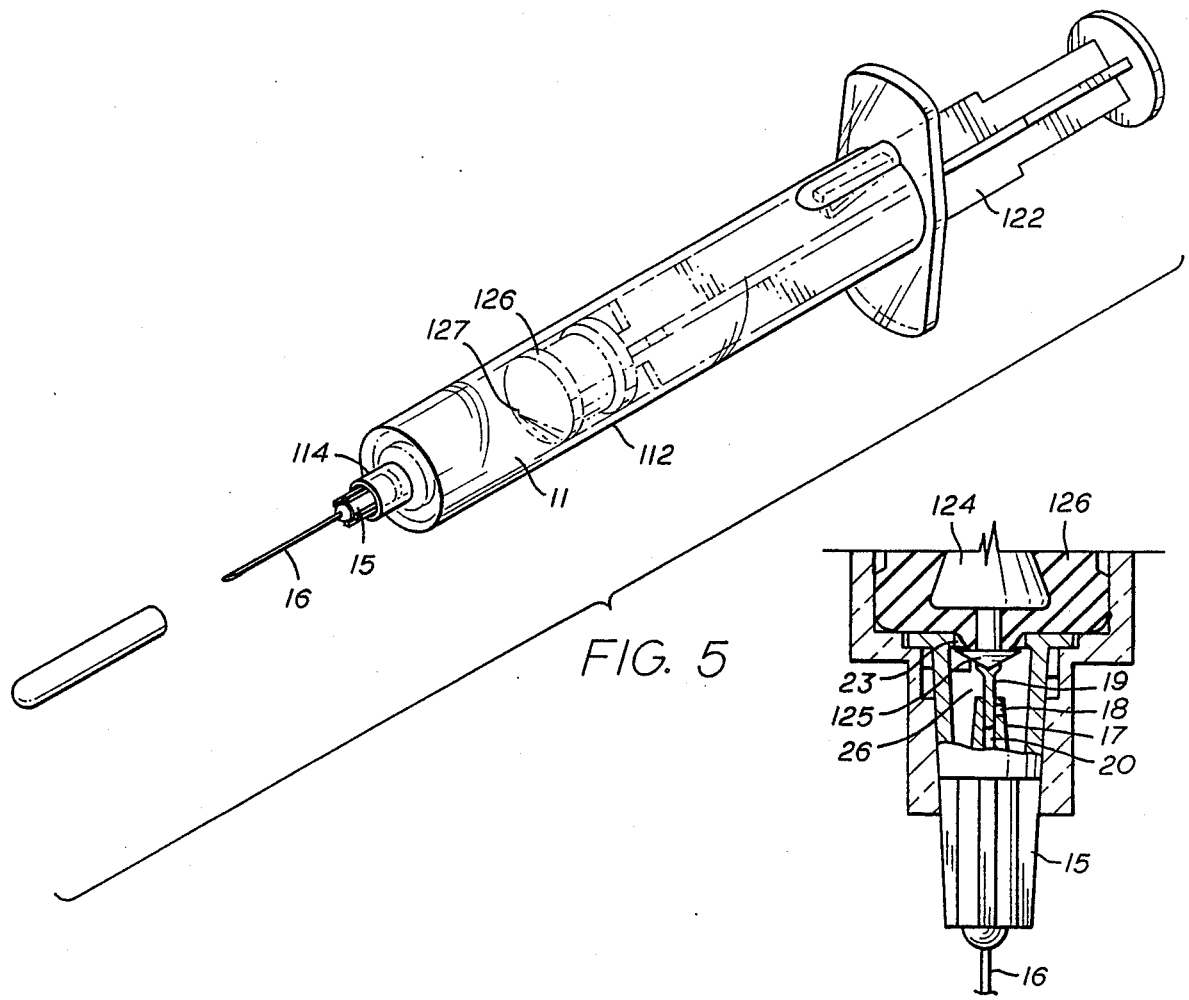
FIG. 5
FIG. 7
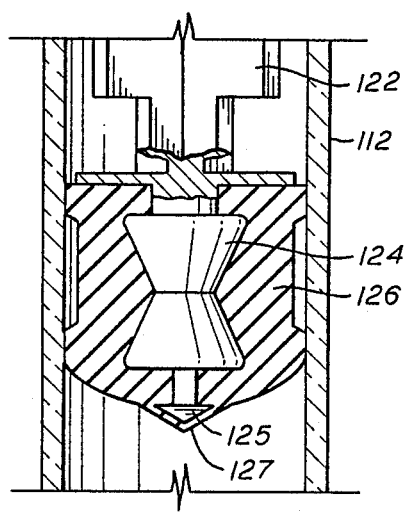
FIG. 6
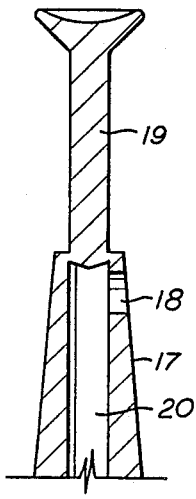
FIG. 8
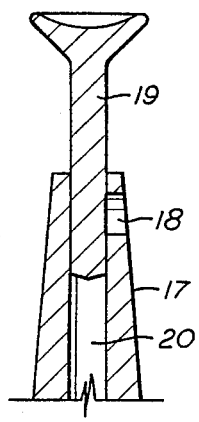
FIG. 9

4,832,693

DISPOSABLE SYRINGE

FIELD OF INVENTION

The present invention relates generally to fluid receivers and dispensers, more particularly to an improved multi-purpose disposable syringe, and most particularly to an improved disposable hypodermic syringe needle.

Hypodermic needle syringes of various types are well known in the medical field. They are used for evacuating fluid, taking fluid samples, giving inoculations and taking blood samples to name a few examples. In particular, when hypodermic needle syringes are used for inoculating against infectious diseases or for taking blood samples from patients suffering from infectious diseases, the reasons for using these syringes only once and then disposing of them become readily apparent. An unfortunate fact is that many of the most infectious diseases are of epidemic proportions in areas of the world where people poorly understand the need for disposing of hypodermic needle syringes after one use. These same have a shortage of syringes. In these countries, when infectious disease is combined with a shortage of training and medical equipment, the unhappy result in many cases will be an ineffective attempt to sterilize what was meant to be a disposable hypodermic needle syringe, and a reuse of that syringe. This leads to further spreading of the very diseases sought to be controlled. Diseases such as AIDS and Serum Hepatitis are obvious examples, but any reuse of a disposable hypodermic needle syringe could lead to Septicemia even where no infectious disease is involved.

This invention renders a hypodermic needle syringe useless immediately upon the completion of its initial use. The need for an auto-destruct hypodermic needle syringe in those parts of the world where education is not a practical solution and where resources are limited is well recognized. This invention provides a device that is based upon existing technologies, that will employ for its manufacture the equipment currently existing, and may be made of the materials that have been determined to be toxicologically safe. This invention will be capable of being used by health personnel after minimal training, and it will not be capable of being reused. This invention is a self-destruct mechanism that requires no voluntary action by the user and prohibits misuse or tampering with the hypodermic needle syringes to make them reusable. This invention is therefore ideally suited for use as an adaptation to syringes of many different types that will be used in places where there is a danger of recycling syringes. An additional advantage is that inasmuch as this invention will render a hypodermic needle syringe useless after only one use it will minimize the occurrences of infectious diseases spread by recycling needles even in those countries where the dangers are known, by preventing the use by those such as drug addicts.

SUMMARY OF THE PRESENT INVENTION

The present invention solves the problems presented by the present state of the art in a simple manner. What is provided is a hypodermic needle syringe tht may be of any of the usual designs, having a barrel section provided with an opening and flanges at one end and provided with a fluid passage and needle support at the opposite end and having a piston plunger. The open flanged end of the syringe barrel receives the piston plunger for movement down the syringe barrel. The auto-destruct means provided by this invention provides an improvement for disposable hypodermic needle syringes of all types. The auto-destruct means is located at the forward end of the hypodermic needle syringe barrel and has comprised of a pedestal fixed to the needle support member both of which have fluid passages communicating through the needle and on into the fluid cavity of the syringe barrel. The pedestal fixed to the needle support member is further provided with an opening through the side of the pedestal in communication with the fluid cavity of the syringe barrel. A plug is provided and inserted into the upper opening of the fluid passage provided in the pedestal which is fixed to the needle support member. The plug that is inserted into the opening of the pedestal either protrudes into the fluid cavity of the syringe barrel or a protruberance is provided on the forward end of the piston head that will extend past the fluid cavity and out of the end of the syringe barrel when the plunger is completely depressed on the injection stroke of the hypodermic needle syring. Upon the completion of one injection stroke of the plunger either the forward surface of the piston head or the stinger attached to the forward piston of the piston head will press the plug inserted into the pedestal into the fluid passage thereby blocking the opening in the side of the pedestal and permanently sealing the fluid passage. This simple and economical means is a solution to the problem of the present art and attains the object of the present invention in that it automatically renders a hypodermic needle syringe useless after its first use. Therefore, no matter what the incentive, no further use can be made of a syringe equipped with this auto-destruct improvement and the hypodermic needle syringe must be disposed of, thereby preventing the transfer of infectious diseases.

BRIEF DESCRIPTION OF THE DRAWINGS

FIG. 5 is a perspective view of an alternative syringe also equipped with the auto-destruct mechanism of this invention.

FIG. 6 is a longitudinal section through the middle portion of the hypodermic needle syringe barrel of FIG. 5.

FIG. 7 is a longitudinal section through the forward end portion of the hypodermic needle syringe of FIG. 5.

FIG. 8 is a detailed sectional view of the pedestal, fluid passage and plug of the present invention.

FIG. 9 is another sectional detailed view of the pedestal, fluid passage, and plug of the present invention.

DETAILED DESCRIPTION OF THE PREFERRED EMBODIMENT

Figure 1:
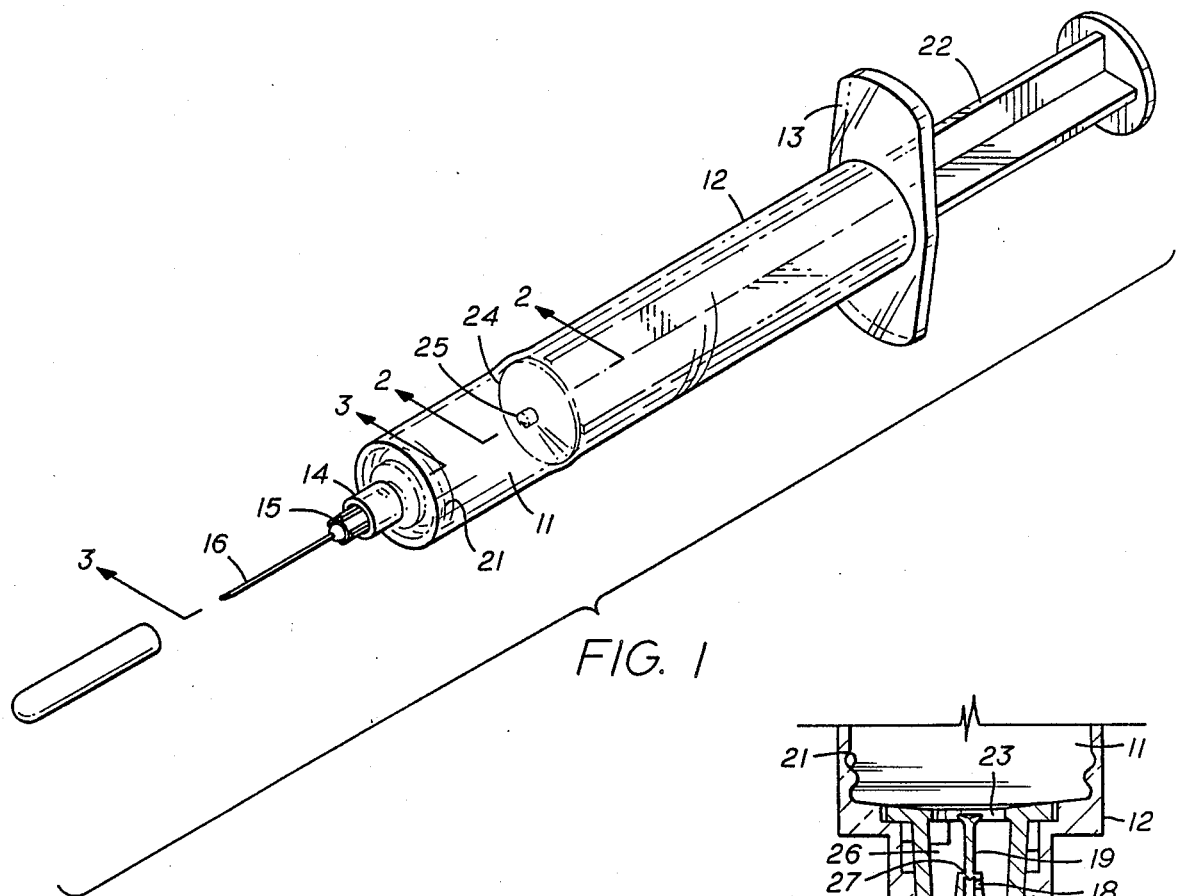
FIG. 1 is a perspective view of a typical syringe that is equipped with the auto-destruct mechanism.
Figure 2:
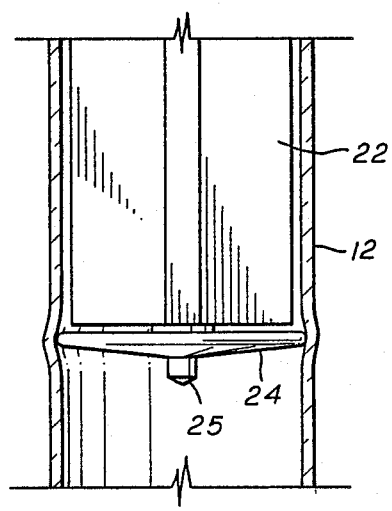
FIG. 2 is a longitudinal section of the middle portion of the barrel of the syringe of FIG. 1.

Referring now to the drawings, the present invention will now be described in detail. Referring particularly to FIG. 1, a multi purpose hypodermic needle syringe is illustrated. It will be noted that this syringe is of the type that utilizes a resilient barrel 12 that deforms as the harder piston head 24 progressively passes along its inner surface. FIG. 2. The attributes of a standard syringe are illustrated in FIG. 1. In particular is illustrated the plunger 22, the syringe barrel 12, and the needle collar 14. Also illustrated are the flanges 13 attached to the rearward end of the syringe barrel. The present invention however is not to be understood as limited to hypodermic needle syringes of this type. For example an alternative syringe design is depicted in FIG. 5. It will be noted that this hypodermic needle syringe is of the somewhat more common configuration utilizing a rigid barrel 112 and a resilient piston plug 126. FIG. 6 Despite the two examples of syringe types illustrated, it will be obvious that the present invention, as will be described below, is widely adaptable to many other variations of hypodermic needle syringes, and it is not to be understood as being limited to those illustrated. In particular this invention will work well with some of the newer design syringes with retractable needles.

Returning now to the drawings and referring again particularly to FIG. 1, there is illustrated the improved disposable syringe. Any syringe of the usual manufacture may be improved by the addition of this invention. Depicted in FIG. 1 is longitudinal section 3—3, taken through the forward end portion of the syringe. The section 3—3 is illustrated in FIG. 3.

Figure 3:
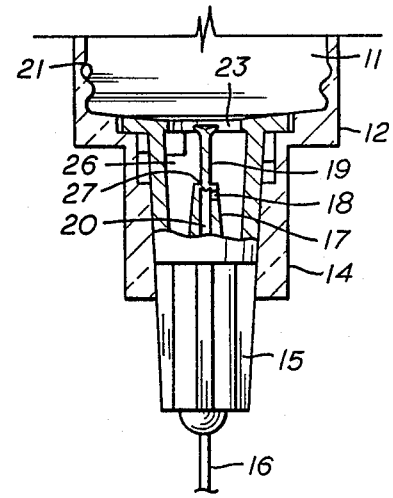
FIG. 3 is a longitudinal section of the forward portion of the hypodermic needle syringe of FIG. 1.

FIG. 3 illustrates in detail the forward end of the barrel 12, the barrel fluid cavity 11, the needle support member 15, the needle 16 and the pedestal 17, fluid passage 20, and solid plug 19, of this invention. The needle support member 15 is provided with an interior well 26 that is open to the fluid cavity 11 of the syringe barrel 12 when the support member 15 is fixed within the collar 14. The needle support, within the previously mentioned well, is further provided with a pedestal 17, fluid passage 20 and plug 19. Although in both of the embodiments illustrated the needle support member is installed from the inside of the syringe barrel, this invention can obviously be adapted so that the needle support member attaches to the outside of the syringe barrel. It should be noted that the primary components of the invention mentioned so far, those being the pedestal 17, fluid passage 20, and plug 19, are located within a standard size needle support member 15, and therefore may be used in any syringe that accepts a standard needle support member. The pedestal 17, and plug 19 may be formed of the same material as the needle support member, that is typically of injection molded plastic. The pedestal 17 as illustrated is in the shape of truncated cone, and the plug 19 is formed approximately in the shape of a golf tee. The pedestal 17 and solid plug 19 will be most efficiently produced in an injection molding process and therefor the specific shapes may be tailored to facilitate that efficient production. The method of molding the needle support member 15, the pedestal 17 with fluid passage 20, and plug 19 may provide for molding all of these components as a single piece. The operation of the plug and the pedestal unit will be such that when the plug is pressed forward, the plug to pedestal interface 27 will either shear to allow the plug to be pressed further into the fluid passage 20, or the pedestal will collapse on itself. Either failure mode will seal the fluid passage 20 as desired. FIGS. 8 and 9. The thickness of the pedestal 17, plug 19, and plug to pedestal interface 27 are selected to provide the above described operation. The fluid passage 20, as illustrated, is a passage bored or formed in the molding process through the longitudinal axis of the pedestal. The fluid passage also has at least one opening 18 through the side of the pedestal 17. Therefore the fluid passage through the needle 16 and support 15 is extended through the raised pedestal and exits through the hole 18 in the side of the pedestal 17 into the well 26 which commununicates with the fluid cavity 11 of the syringe barrel 12. The side opening may also be formed in the molding process. The plug 19 is manufactured to an outside diameter that is essentially the same diameter as the passage 20 through the pedestal 17. The unit comprised of the needle 16, needle housing 15, pedestal 17, and plug 19 will be provided by a manufacturer with the plug 19 inserted into the fluid passage 20, but not pressed into the passage 20 far enough to block the side opening 18. When, as will be described below, the plug 19 is pressed deeper into the fluid passage 20 by either the forward end of the piston head 24, 126 or a stinger 25, 125 fixed to the forward end of the piston head 24, 126 the plug will seal the side opening 18 and prevent any further movement of fluid through the passage 20 or side opening 18.

As mentioned in the proceeding paragraph the plug 19 is pressed into the fluid passage 20 by the forward end of the piston head 24, 126 upon the completion of the first full injection stroke of the plunger 22, 122. In both of the illustrated embodiments, the needle support member 15 is located within a collar 14, 114 fixed to the forward end of the barrel 12, 112. This is a common method of manufacture, and due to the resulting location of the pedestal 17 forward of the forward end of the barrel 12, 112 and consequently out of the reach of the piston head 22, 126 itself, in the two embodiments illustrated the piston head 24, 136 is provided with a stinger 25, 125 that upon completion of a full injection stroke of the plunger 22, 122 will protrude forward of the end of the barrel 12 and press the plug 19 further into the pedestal 17 thereby sealing the fluid passage 20 and side opening 18. FIGS. 2, 4, 6 and 7. Although not illustrated, it is obvious that the pedestal 17 and the plug 19 could be manufactured so as to protrude into the fluid cavity 11 of the barrel 12 thereby eliminating the need for a stinger 25, 125 on the forward end of the piston head.

Figure 4:
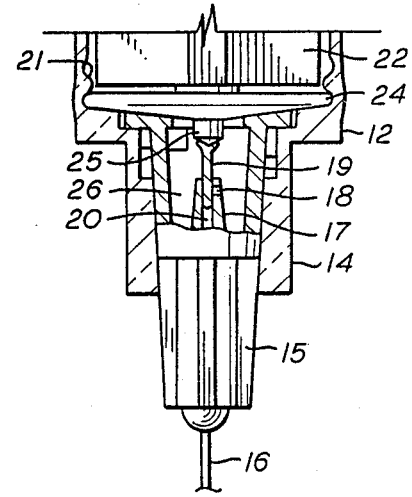
FIG. 4 is a sectional view of a longitudinal section through the forward portion of the hypodermic needle syringe of FIG. 1.

As illustrated in FIGS. 1 and 4 the resilient syringe barrel of the syringe illustrated in FIG. 1 is provided with a notched detent 21 in the forward interior portion of the barrel to gage the distance of the piston head from the forward end of the barrel. This notched detent 21 is located so that when the edge of the piston head 24 is seated within the notch the stinger 25 will not contact the plug 19. This detent is provided for assembly and shipping purposes so that when the plunger and piston head assembly is inserted into the barrel during manufacture the plug 19 will no inadvertently be pressed into the pedestal 17 thereby destroying the usefulness of the hypodermic needle syringe before its initial use.

The embodimemt illustrated in FIGS. 5, 6 and 7 utilizes a resilient piston plug 126 as mentioned previously. As illustrated in FIG. 6 the plunger stem 122 is formed at it forward end to a stinger 125 and an hour glass shaped piston head carrier 124. The piston head 126 of this embodiment is formed of a soft resilient substance, such as butyl or latex for example, and the forward end of the piston head 126 is formed as a thin diaphragm 127 which covers the stinger until the completion of the first full injection stroke. This diaphragm should be thick enough to require a moderate amount of force before the stinger 125 punctures the diaphragm. Similar to the detent 21 provided in the embodiment of FIG. 1, this will aid in manufacture and shipping in that the hypodermic needle syringe can be assembled easily without fear of inadvertently pressing the plug 19 further into the pedestal 17 therby blocking the fluid passage and destroying the usefulness of the syringe prior to its initial use. During its initial use, upon the completion of the first full injection stroke, the piston head 126 will bottom against the forward end of the barrel 12, 112 but the stinger 125 will break through the thin diaphragm 127 and protrude through the opening 23 and press the plug 19 into the fluid passage 20 provided in the pedestal 17 thereby sealing the passage 20 and side opening 18 and rendering the syringe or at least the syringe needle useless.

OPERATION OF THE IMPROVED DISPOSABLE SYRINGE

It is anticipated that the auto-destruct disposable hypodermic needle syringe will be shipped and packed in a sterile wrapper as is usual in the medical field. The syringes will be shipped collapsed, with the FIG. 1 embodiment having the piston head 24 positioned in the forward detent 21 provided at the forward end of the barrel 12 and the FIG. 6 embodiment having the resilient piston plug 126 bottomed against the forward end of the barrel 112, but without the stinger 125 protruding into the opening 31. The hypodermic needle syringe will be removed from the sterile wrapper, and the needle 16 inserted into the object from which fluid is to be drawn. The plunger 22, 122 and attached piston head 24, 126 will then be drawn to the rear of the syringe, creating a suction that pulls fluid through the needle 16 and through the fluid passages 20 into the fluid cavity 11. The needle is then withdrawn from the first object filled with fluid. The needle of the filled syringe can next be inserted into the object to be injected with the fluid substance, and the plunger 22, 122 and the attached piston head 24, 126 will be moved in the forward direction on the injection stroke. During the injection the fluid is forced by the piston head 24, 126 out of the barrel cavity 11 through the fluid passage 20 and through the needle 16 into the object being injected. FIG. 8. The injection stroke is completed with the piston head snaps past the detent 21 on the FIG. 1 embodiment and the stinger 25 presses the plug 19 into the pedestal 17 permanently sealing to the fluid passage 20 and side opening 18. FIG. 9 the hypodermic needle syringe is thereby rendered useless and must be discarded.

The FIG. 5 embodiment operates similarly on the suction and injection strokes of the piston head. FIGS. 8 and 9. Upon the completion of the injection stroke the resilient head 126 bottoms against the forward end of the syringe barrel and the stinger 125 protrudes through the opening 31, forces the plug 19 further into the pedestal 17 permanently sealing the fluid passage 20 and the side opening 18. FIG. 9. The syringe cannot be reused and must be discarded.

It should be noted that it will be possible to supply the hypodermic needle syringe as a single unit in which the syringe barrel cannot be disconnected from the needle support member. This would prevent any reuse of the barrel and plunger as well as the hypodermic needle.

Because many alternative embodiments may be made within the scope of the invention herein disclosed, it is to be understood that details herein are to be interpreted as illustrative and not in a limiting sense. Numerous other alternatives will become readily apparent to those of ordinary skill in the art in the light of the teachings of this specification.

What is claimed is:

1. An improved disposable syringe comprising; a barrel having an inner cavity, a fluid passage at its forward end, and an opening rearward end; a plunger, provided with a piston head, received into the rearward end of the barrel and carried within the barrel in slidable sealing engagement with the inner wall of the barrel, between forward and retracted positions; an auto destruct fluid seal means disposed at the forward end of the barrel that permanently seals the fluid passage upon the first complete injection stroke of the syringe, said auto-destruct fluid seal means comprising:
    (a) a raised pedestal provided with a fluid path forming the fluid passage at the barrel's forward end, said pedestal projecting into the cavity of the barrel at the forward end of the syringe and;
    (b) disposed atop the pedestal, a raised plug which is pressed into the pedestal by the forward surface of the piston head when the plunger is fully depressed and the piston head moves to its most forward position, thereby permanently blocking the fluid path.

2. An improved disposable syringe comprising; a barrel having an inner cavity, a fluid passage at its forward end, and an opening at its rearward end; a plunger, provided with a piston head, received into the rearward end of the barrel and carried within the barrel in slidable sealing engagement with the inner wall with the barrel, between forward and retracted pistons; wherein the fluid passage at the syringe barrel forward end comprises:
    (a) a collar projecting from and fixed to said forward end of the syringe barrel;
    (b) said collar adapted to sealingly receive and retain a needle support member, which has a well open to the inner cavity of the syringe barrel;
    (c) said well disposed forward of the forward end of the syringe barrel when the needle support is sealingly mounted within the collar;
    (d) said needle support member mounts a hypodermic needle;
    (e) said needle provided with a fluid path which extends through a raised pedestal which is formed inside the well of the needle support member with the fluid path through the pedestal;
    (f) a solid cylindrical plug of the same diameter as the fluid path provided through the pedestal, said plug pressed into the fluid path opening through the top of the pedestal within the well of the needle support member so that it seals the path through the top of the pedestal but does not extend deep enough into the pedestal to obstruct the opening provided through the side of the pedestal.

3. The invention of claim 1 wherein:
    (a) the injection piston head is more rigid than the barrel and said piston head is of a diameter slightly greater than the inside diameter of the barrel so that the piston head will slightly stretch said barrel throughout the travel of the piston head on suction and injection strokes, and wherein;
    (b) the barrel is provided with detent means to gage the distance of the piston head from the forward end of the syringe barrel and to releasably catch the piston head before said head makes a complete injection stroke and before said head makes contact with the raised solid plug positioned in the fluid passage provided in the pedestal.

4. The invention of claim 3 wherein the detent means is comprised of a shallow groove formed around the inside circumference of the syringe barrel near the forward end but at a distance sufficient to keep the forward part of the piston head from contacting the solid plug when the piston head is positioned within said groove.

5. The invention of claim 2 wherein:
   (a) the injection piston head is more rigid than the barrel and said piston head is of a diameter slightly greater than the inside diameter of the barrel so that the piston head will slightly stretch said barrel throughout the travel of the piston head on suction and injection strokes, and wherein;
   (b) the barrel is provided with detent means to gage the distance of the piston head from the forward end of the syringe barrel and to releasably catch the piston head before said head makes a complete injection stroke and before said head makes contact with the raised solid plug positioned in the fluid passage provided in the pedestal;
   (c) the piston head is provided with a protrusion at the forward surface so that when the piston is pressed into the most forward position the protrusion will reach forward of the forward end of the barrel and into the needle support well a distance sufficient to press the solid plug deep enough into the raised pedestal to seal the fluid opening in the side of the pedestal.

6. The invention of claim 5 wherein the detent means is comprised of a shallow groove formed around the inside circumference of the syringe barrel near the forward end but at a distance sufficient to keep the protrusion of the forward part of the piston head from contacting the solid plug when the circumference of the piston head is positioned within said groove.

7. The invention of claim 1 wherein:
   (a) the piston head is formed of a resilient material that is relatively softer and more flexible than the barrel;
   (b) said piston is provided with a receptacle of a particular shape molded into the head which is mounted to the forward end of the plunger which is formed to a corresponding shape;
   (c) said plunger further includes at its most forward end a protrusion that upon the conclusion of the first injection stroke of the piston will be forced through the forward surface of the piston head which is so formed as to be relatively thing and membranous where said piston head is in contact with the protrusion;
   (d) so that when the piston head bottoms against the rearward end of the syringe barrel at the completion of its injection stroke the protrusion formed at the forward end of the plunger will part the membranous portion of the piston head and thereby will extend forward of the end of the syringe barrel and far enough into the well of the needle support to press the solid plug deep into the raised pedestal a distance sufficient to obstruct the side opening and thereby block the fluid passage and render the syringe useless.

* * * * *